US006814852B2

(12) United States Patent
Holstun et al.

(10) Patent No.: US 6,814,852 B2
(45) Date of Patent: Nov. 9, 2004

(54) GENERATION OF GAS IN A LAB-ON-A-CHIP ENVIRONMENT

(75) Inventors: Clayton L. Holstun, San Marcos, CA (US); David Tyvoll, La Jolla, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 61 days.

(21) Appl. No.: 10/196,605

(22) Filed: Jul. 15, 2002

(65) Prior Publication Data

US 2004/0007456 A1 Jan. 15, 2004

(51) Int. Cl.[7] .................................................. C25C 1/00
(52) U.S. Cl. ...................... 205/615; 205/628; 205/633; 205/637; 204/242; 204/275.1; 204/278
(58) Field of Search ............................... 205/615, 628, 205/633, 637; 204/242, 275.1, 278

(56) References Cited

U.S. PATENT DOCUMENTS

| | | |
|---|---|---|
| 3,894,538 A | 7/1975 | Richter |
| 4,202,740 A | 5/1980 | Stoner et al. |
| 4,563,249 A | 1/1986 | Hale |
| 5,593,552 A | 1/1997 | Gordon et al. |
| 5,705,050 A | 1/1998 | Sampson et al. |
| 5,992,820 A | 11/1999 | Fan et al. |
| 6,168,948 B1 | 1/2001 | Anderson et al. |
| 6,283,440 B1 * | 9/2001 | Evans .......................... 251/11 |
| 2002/0009015 A1 * | 1/2002 | Laugharn et al. ........... 366/108 |
| 2003/0150716 A1 * | 8/2003 | Hua et al. .................... 204/232 |

FOREIGN PATENT DOCUMENTS

| | | |
|---|---|---|
| EP | 0993836 | 4/2000 |
| WO | WO 01/70381 | 9/2001 |
| WO | WO0185328 | 11/2001 |
| WO | WO03046256 | 6/2003 |

OTHER PUBLICATIONS

Ep search report—for EP 03 254259 dated Feb. 6, 2004.

* cited by examiner

Primary Examiner—Wesley A. Nicolas (57) ABSTRACT

The present invention is drawn to the electrolysis of fluids in a lab-on-a-chip environment for generating gases. Various lab-on-a-chip embodiments are described along with a method of generating gas in a lab-on-a-chip environment. The method comprises the steps of (a) providing a substrate having active circuitry thereon, at least a portion of said active circuitry being readable by a computer; (b) providing an electrolytic cell configured for communication with the active circuitry, said electrolytic cell comprising an anode and a cathode in an electrolytic fluid bath; and (c) generating a gas in the electrolytic fluid bath by creating an electrical potential between the anode and the cathode through the electrolytic fluid bath.

48 Claims, 6 Drawing Sheets

GENERATION OF GAS IN A LAB-ON-A-CHIP ENVIRONMENT

FIELD OF THE INVENTION

The present invention is drawn to the generation of gas in a lab-on-a-chip environment. More specifically, the present invention is drawn to the electrolysis of fluids in a lab-on-a-chip environment for generating gases.

BACKGROUND OF THE INVENTION

A "lab-on-a-chip" can include systems for metering, measuring, and/or mixing small liquid samples with reagents, moving the mixtures to an integrated, temperature controlled reaction chamber, separating compositions, and/or determining results with an onboard detector. At first, lab-on-a-chip technology focused mainly on the analysis of substances, but has evolved to include a wider range of possibilities. For example, the synthesis of products to determine and/or research their properties can be implemented. There are several areas where lab-on-a-chip technology is of interest today, including the research areas of analysis, chemical reaction, chemical and pathogen detection, genetic research, micro/nanofluidics, and chemical and pathogen detection.

Miniaturization is a trend in chemistry that has generated considerable interest over the last few years. This is in part because of some sound commercial reasons for wanting to move to smaller-scale synthesis and analysis, including high sample throughput, pressure to reduce costs, and increasingly stringent environmental regulations. Laboratory methods in use today may not be competitive in the long run as the desire for chemical processes become smaller, cleaner, cheaper, and faster. Advantages that are driving technology in this direction include the fact that power consumption and reagent costs can be reduced with such methods, less laboratory space is required, devices can be portable for on-site use or placed in previously restricted spaces, analysis procedures can be automated or made in parallel increasing sample and product throughput, and performance can be enhanced leading to better yields and faster analysis.

Though trends are leading to miniaturizing chemical processes, such as with lab-on-a-chip technology, many known chemical processes require the presence of certain reagents, often in gaseous form. Chemical processes carried out on a chip are no different. And while many methods exist for storing and moving liquids on a small chip, storing and moving gases is much more difficult. Thus, it would be desirable to provide systems and methods for generating and utilizing gases in the context of lab-on-a-chip technology for various purposes.

SUMMARY OF THE INVENTION

It has been recognized that rather than storing gases on a lab-on-a-chip, it would be desirable to provide a process of creating gases from liquid source chemicals, such as through electrolysis. It has also been recognized that related processes of fluid movement or injection can also provide advantages in lab-on-a-chip technologies.

Specifically, an integrated lab-on-a-chip system for generating gases can comprise a substrate having active circuitry thereon, wherein the active circuitry is configured for communication with an electrolytic cell. The electrolytic cell can comprise a housing defining an electrolyte fluid chamber containing an anode and cathode as part of the circuitry and a gas collection chamber, and an electrolyte fluid contained within the electrolyte fluid chamber. The anode and cathode are positioned in the chamber to be in contact with the electrolyte fluid, wherein upon completion of the circuit the anode and cathode can generate a gas from the electrolyte fluid. Upon creating of the gas, collection and/or storage in the gas collection chamber can occur. In order to utilize the gas, it is desirable to have a port for fluidically connecting the gas collection chamber to another chamber or the atmosphere.

In another embodiment, an integrated lab-on-a-chip system for generating gases can comprise a substrate having active circuitry thereon, wherein the active circuitry is configured for communication with an electrolytic cell. The electrolytic cell can comprise a housing defining an electrolyte fluid chamber, and an electrolyte fluid contained within the electrolyte fluid chamber. An anode and a cathode can be positioned in contact with the electrolyte fluid, wherein the anode and cathode are configured for generating a gas from the electrolyte fluid. By simple or more complex fluid displacement systems, the generated gas can be used to provide movement of a working fluid, e.g., the electrolyte fluid itself or a secondary fluid.

In a related embodiment, a method of generating gas in a lab-on-a-chip environment can comprise the steps of (a) providing a substrate having active circuitry thereon, wherein at least a portion of the active circuitry is readable by a computer; (b) providing an electrolytic cell configured for communication with the active circuitry, wherein the electrolytic cell comprises an anode and a cathode in an electrolytic fluid bath; and (c) generating a gas in the electrolytic fluid bath by creating an electrical potential between the anode and the cathode through the electrolytic fluid bath.

DETAILED DESCRIPTION OF THE PREFERRED EMBODIMENT(S)

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. Further, before the preferred embodiments of the present invention are disclosed and described, it is to be understood that this invention is not limited to the particular process steps and materials disclosed herein as such process steps and materials may vary to some degree. It is also to be understood that the terminology used herein is used for the purpose of describing particular embodiments only and is not intended to be limiting as the scope of the present invention will be limited only by the appended claims and equivalents thereof.

As used in this specification and the appended claims, singular forms of "a," "an," and "the" include plural referents unless the content clearly dictates otherwise.

"Lab-on-a-chip" can include any chip-like system or device that can be controlled by a computer, carries out a chemical process, and feeds data back to a computer or has an external measurement system. Examples of uses of such chips include metering, measuring, moving, and/or mixing microscopic fluid samples, including gases. For purposes of the present invention, a lab-on-a-chip includes a substrate having active circuitry thereon that interfaces with an electrolytic chemical cell.

"Active circuitry" includes traces and digital or analog elements such as transistors, resistors, diodes, capacitors, and the like. Active circuitry can be present on a substrate and/or an electrolytic cell housing, can interface with a computer, and interfaces with an electrolytic cell. For example, active circuitry can be used to heat or cool liquids, create vapor bubbles, detect the presence of an ionic, biological, or other chemical or biological species, e.g., DNA, control electricity of the anode/cathode, or excite and/or measure fluorescence.

"Electrolysis" or "electrolytic reaction" is an electrochemical reaction that utilizes an electrolyte, a cathode, an anode, and a source of electricity. A reduction-oxidation (redox) reaction causes the decomposition of the electrolyte, and can result in the production of gases. The electrolyte is typically a solution containing free moving ions, such as acid, base, or salt solutions. Ionic liquids can also be used. When an electrical potential is applied across the electrodes, the cathode becomes negatively charged and the anode becomes positively charged. The positive ions in the electrolyte move towards the cathode, where they receive an electron (reduction). The negative ions in the electrolyte move towards the anode, where they donate an electron (oxidation). The external voltage source completes the circuit. The reaction is increased when the concentration of ions is increased, the voltage is increased, or the distance between the electrodes is decreased.

"Electrolysis cell" or "electrolytic cell" can comprise electrodes, e.g., an anode and a cathode, an electrolyte fluid, a source of electricity, one or more fluid containing chamber(s), and optionally, membranes or other barriers, and/or devices such as pumps, valves, accumulation chambers, reaction chambers, or the like. Other components can be present as would be known to one skilled in the art after reading the present disclosure.

"Computer" includes any device that communicates with active circuitry of the lab-on-a-chip and provides accessible data to a user or other device.

Figure 1:
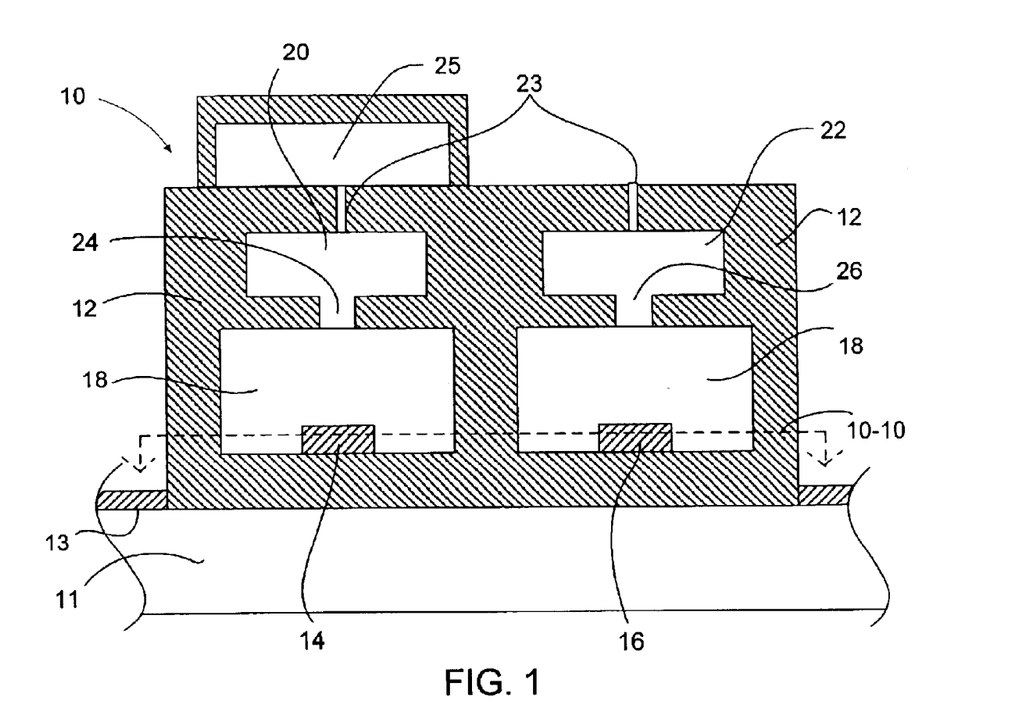
FIG. 1 is a cross-sectional schematic diagram of a lab-on-a-chip for generating and collecting gases in accordance with an embodiment of the present invention.
Figure 2:
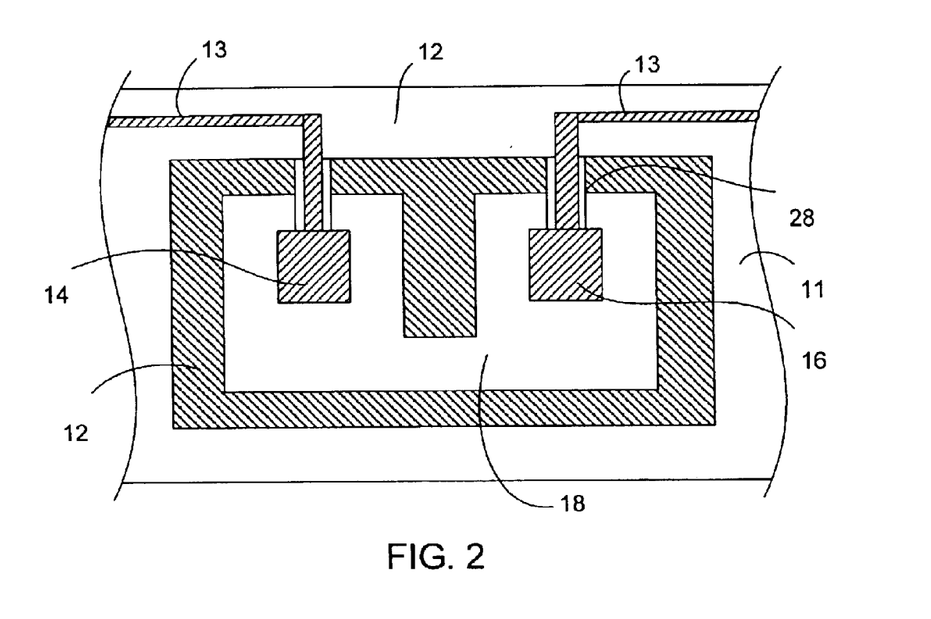
FIG. 2 is an alternative cross-sectional schematic diagram of the lab-on-a-chip of FIG. 1 taken along line 10—10.

Turning now to FIGS. 1 and 2, which depict a schematic of an exemplary embodiment of a lab-on-a-chip arrangement of the present invention, a lab-on-a-chip system 10 is shown having a chip substrate 11 connected to an electrolytic cell housing 12. The housing 12 defines various chambers. One of the chambers is a fluid chamber 18 for holding an electrolytic fluid. Exemplary fluids can include water, ionic liquids, and various salt solutions thereof. In practice, salts can be added to water to increase the electrical conductivity, which enhances the rate of electrolysis. In addition to these exemplary electrolytic fluids, any fluid can be used that provides a desired gas upon electrolysis. In order to effectuate electrolysis, an anode 14 and a cathode 16 are present, and are electrically powered by a power source (not shown) via active circuitry 13. Any power source such as would typically be used to power a computer chip can be used herein. In the embodiment, as shown in FIG. 2, an insulator 28 is present that structurally connects the anode 14 and the cathode 16 to the housing 12, though this is not required. By creating electrical potential between the anode and the cathode through the electrolytic fluid, one or more gases can be collected in the first gas collection chamber 20 and/or the second gas collection chamber 22 through a first gas window 24 and/or a second gas window 26, respectively. Ports 23 are present for injecting reactants or other material into the gas collection chambers 20, 22, or for transporting the one or more gases outside the gas collection chambers 20, 22 for use. For example, a biological culture chamber 25 can be present for growing cell cultures with generated oxygen in one embodiment.

Electrolysis of a fluid solution can generate gases. To the extent that the gases are insoluble in the fluid, they will form sustainable bubbles. To illustrate an example wherein the embodiment shown in FIGS. 1 and 2 (and subsequent embodiments) can be used, the electrolysis of water ($H_2O$) can be considered. With water, two molecules decompose to one oxygen molecule at the anode, and two hydrogen molecules at the cathode. An aspect of this reaction is that two bubbles are formed, one of hydrogen and one of oxygen. The ratio of the number of molecules of each is determined by the stoichiometry and electrochemical potential of the electrolyte: two hydrogen molecules for every oxygen molecule. In the case of water, hydrogen and oxygen have low solubilities, and therefore the bulk of the gases generated from the electrolysis of water will form discrete bubbles. The ratio volumes of the bubbles will be very nearly 2 to 1, as predicted by the ideal gas law.

In further detail, if water is the electrolyte chosen, the electrolysis of water is generally known to occur as follows. At the anode, water is oxidized ($2H_2O \rightarrow O_2 + 4H^+ + 4e^-$); and at the cathode, water is reduced ($4H_2O + 4e^- \rightarrow 2H_2 + 4OH^-$). The net reaction is $6H_2O \rightarrow O_2(g) + 2H_2(g) + 4H^+ + 4OH^-$, and requires 4 electrons. The flow of 4 moles of electrons will produce 1 mole of oxygen gas, and 2 moles of hydrogen gas. The flow of 1 mole of electrons will produce 0.25 moles of oxygen gas and 0.5 moles of hydrogen gas. One Faraday is the amount of charge in 1 mole of electrons. One Faraday is equal to 96,500 Coulombs. Therefore, 1 Coulomb is the amount of charge in $1 \times 10^{-5}$ Faraday. A current of 1 ampere produces a charge flow of 1 Coulomb per second. A current of 1 ampere produces a charge flow of $1 \times 10^{-5}$ Faradays per second, or $1 \times 10^{-5}$ moles of electrons per second. A current of 1 ampere produces oxygen gas at the rate of $0.25 \times 10^{-5}$ moles per second. A current of 1 ampere produces hydrogen gas at the rate of $0.5 \times 10^{-5}$ moles per second. Using the ideal gas law, at 25° C.: 1) a current of 1 ampere produces oxygen gas at the rate of 0.063 cm³ per second; and 2) a current of 1 ampere produces hydrogen gas at the rate of 0.127 cm³ per second.

With respect to issues related to volume ratios of liquid compared to gas, again, using water as an example, 1 mole of water has a mass of about 2(1.0)+1(16.0), or 18.0 grams. Using a density of 1 g/cm³, 1 mole of water in the liquid state has a volume of 18 cm³. Conversely, using the ideal gas law, one mole of water in the vapor state also has a mass of 18.0 grams, but a volume of 24,500 cm³ at 25° C. and one atmosphere. Thus, a small amount of liquid water can be converted to a large amount of vapor by volume, at more than a 1300:1 ratio.

In an alternative example, the electrolysis of sodium chloride solutions can be considered. Specifically, sodium chloride can be dissolved in water where it dissociates into $Na^+$ and $Cl^-$ ions. Depending on the concentration of dissolved sodium chloride, different gases will be produced during the electrolysis. At low concentrations, hydrogen and oxygen gases will be produced. At high concentrations, hydrogen and chlorine gases will be produced. At intermediate concentrations, hydrogen and both chlorine and oxygen gases will be produced. Other halogen gases such as bromine and iodine can be similarly produced as would be known by those skilled in the art after reading the present disclosure.

Using the principles cited above, many electrolytic reactions are possible and can provide many different uses. A unifying principle of an embodiment of the present invention includes the in-situ production of gaseous products using electrolysis in a lab-on-a-chip. The gaseous product could be for reactive purposes, fluid dynamics purposes, for carrying out work, or other possible purposes. Examples of such purposes can be illustrated using the reactions cited above with respect to water and sodium chloride or other similar salts or acids. Simple electrolysis of water produces a stream of oxygen. In, one embodiment, oxygen produced in-situ can be used to sustain cell life where cell life is being cultured on a chip. Conversely, chlorine or bromine gas can be produced to sterilize a chip (for either disposal or reuse).

Another advantage of the present embodiment is the ability to form gases that are difficult to store, as in their gaseous state, some gases can be very reactive. However, in their liquid form they are much more benign. Or it may simply be that the storage of a gas is more difficult than the storing of a liquid. Similarly, a liquid might be very reactive, making its long-term storage in a lab-on-a-chip difficult. By storing these compounds in their less reactive form, and only converting them to the desired form when needed, the shelf life of a lab-on-a-chip can be greatly enhanced. Hydrogen peroxide ($H_2O_2$) provides such an example. Hydrogen peroxide is a very powerful oxidizing agent, and can be generated from a two-step operation where oxygen is first generated by one electrolytic reaction of water, and the oxygen formed is used in another electrode reaction with water (and an electrode catalyst) to form hydrogen peroxide in a different reaction chamber. In particular, hydrogen peroxide can be used for odor control and disinfection, and/or can be used to selectively oxidize certain organic compounds.

Turning to alternative lab-on-a-chip arrangements that would benefit from the production of gas through electrolysis, FIGS. 3–12 are exemplary. Specifically, FIGS. 3–12 depict various embodiments where fluid movement can be effectuated by the production of gas bubbles. There are many reasons why one might want to move fluid on a lab-on-a-chip, but exemplified herein include the movement of a dielectric fluid between capacitors, the movement of a fluid for injection into an adjacent chamber, the movement of multiple fluids to one or more adjacent chambers, and the movement of fluid to effectuate the movement of a mechanical object. Other possible fluid movement can include pumping systems, electrophoresis or dielectrophoresis, for example. The purpose of the present invention is not to set forth every possible lab on a chip arrangement where the formation of bubbles for conducting work, moving fluid, or forming reactive gases would be useful. Rather the present disclosure is focused on the forming of gases through electrolytic processes on a lab-on-a-chip.

There are other methods of forming bubbles other than through electrolysis, such as through thermal creation of bubbles. However, the thermal creation of bubbles is inherently inefficient, and waste heat must be dealt with. For example, with thermal creation of gas bubbles, delicate cells or chromosomes can be damaged by heat or high shear rate. With electrolysis, less energy is needed to create a gas bubble of a given size. For instance, a thermal ink jet printhead can produce a 6 nanogram drop of ink, with a bubble on the order of 12 to 15 picoliters. This requires 1 microjoule of energy for 1.6 microseconds. With a resistance of 140 ohms, this takes about 67 milliamps, which translates to $1.1 \times 10^{-7}$ Coulombs. This amount of electricity corresponds to $1.1 \times 10^{-12}$ moles of electrons. That same number of electrons used to hydrolyze water would produce about 20 picoliters of gas at standard temperature and pressure, which provides some advantage over thermal bubbles with less potentially damaging heat present and far lower shear rates.

More significantly, an advantage of electrolysis formed gas bubbles over thermally grown gas bubbles can be realized when the formation of a sustained gas bubble is desired, e.g., something with a lifetime of more than a few microseconds. Thermally grown bubbles are formed by the vaporization of liquid, and so they collapse quickly when the vapor molecules liquefy. Electrolytically grown bubbles will live until the gas molecules dissolve in the electrolyte, which can be 10 to 1000 times longer than thermally grown bubbles. Additionally, with the use of properly configured electrodes, electrolysis reactions can be reversible. Gas bubbles can be grown, the polarity of the anode and cathode can be reversed, and the gas bubbles can be consumed. Such an arrangement might be useful for pumping and mixing applications.

Figure 3:
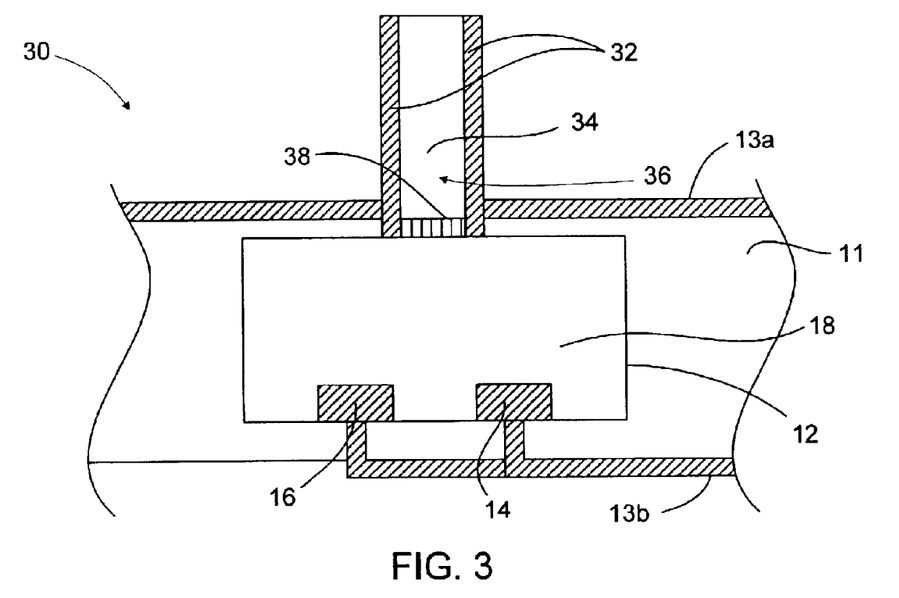
FIG. 3 is a cross-sectional schematic diagram of a lab-on-a-chip with alterable capacitance in accordance with an embodiment of the present invention.
Figure 4:
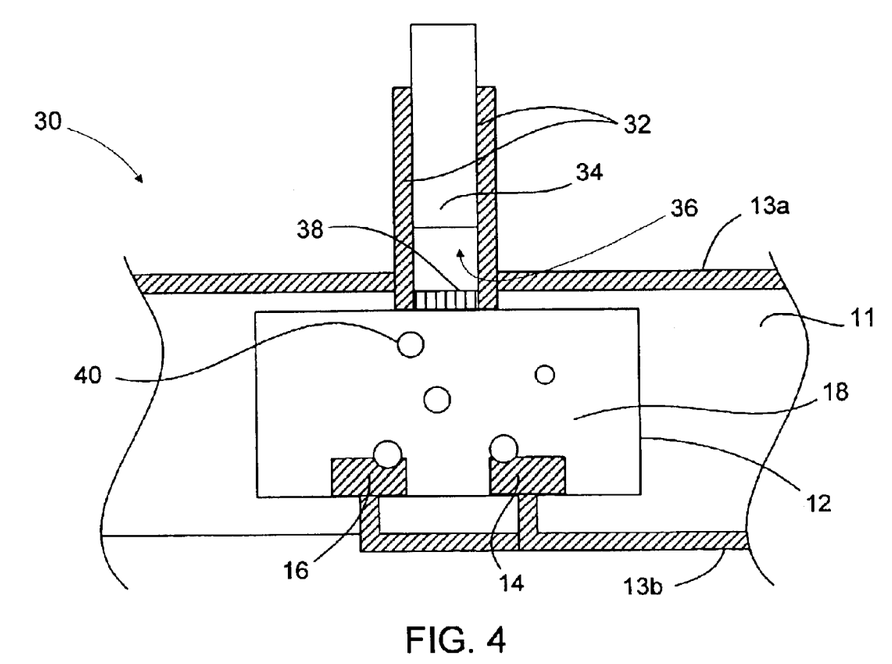
FIG. 4 is a cross-sectional schematic diagram of the lab-on-a-chip of FIG. 3 after at least some generation of gas has occurred.

Turning specifically to FIGS. 3 and 4, a variable capacitor lab-on-a-chip system 30 is shown that is useful as part of an electrical circuit. A chip substrate 11 is present and used to carry active circuitry 13a, 13b. Active circuitry 13b is used to carry power to the anode 14 and the cathode 16. Active circuitry 13a is used to carry signal to and through a capacitance system 32, 34. Housing 12 for holding electrolyte fluid 18 is integrated or etched into the chip substrate 11. The fluid can be any fluid that, when placed under conditions of electrolysis, forms one or more type of gas bubble, preferably of a measurable volume. Again, the anode 14 and cathode 16 function similarly as described previously. Attached to the chip substrate 11, is a pair of plates 32 that define an opening 36. The plates are powered through the active circuitry 13b. Within the opening 36 is a dielectric fluid 34 that provides desired capacitance properties between the plates 32. Optionally, a membrane 38 that is substantially impermeable to the dielectric fluid and substantially permeable to a gas generated by the electrolysis of the fluid within the fluid chamber 18 can be present. As gas bubbles 40 are generated, gas pressure causes the dielectric fluid 34 to become displaced from between the plates 32 (either by movement of the fluid or merely by the presence of gas bubbles in the dielectric fluid). As this occurs, the capacitance properties between the plates 32 is modified.

While thermal ink-jet systems produce a bubble of approximately constant size, an advantage of electrolytic formation of a bubble is that the size can be varied by varying the amount of electricity, e.g., by the number of Coulombs. Additionally, the rate of formation of the bubble can be varied by adjusting the conductivity of the fluid and/or the applied voltage. One application of this is the creation of a variable capacitor as describe above. Bubbles 40 can be used to electrically insulate the two plates 32, driving out the dielectric fluid 34 (or displacing dielectric fluid by the presence of gas bubbles) from between the plates 32. Since the gas collected from the formation of the gas bubbles 40 will have a different dielectric constant than the dielectric fluid 34, and since the size of the gas bubbles 40 can be varied as a function of time and electricity, the presence of a variable capacitor on a chip 30 can result.

Figure 5:
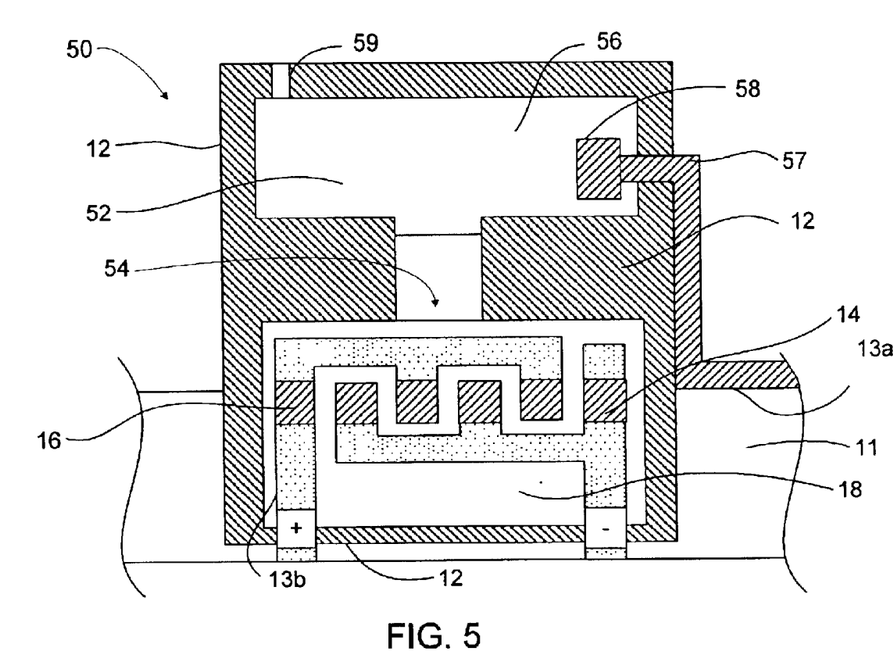
FIG. 5 is a cross-sectional schematic diagram of a lab-on-a-chip configured for injection of a fluid into a chamber in accordance with an embodiment of the present invention.
Figure 6:
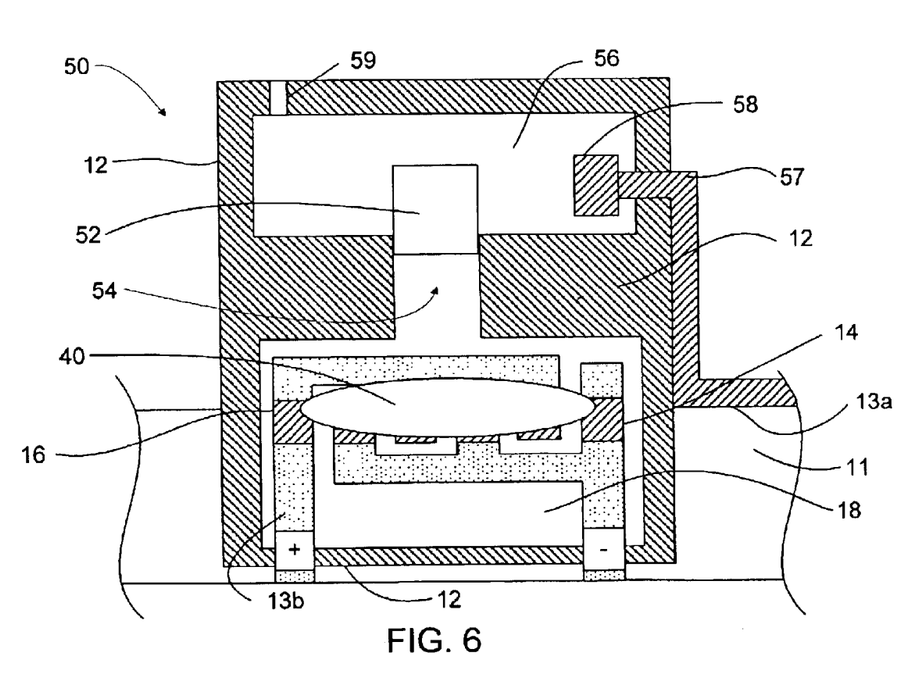
FIG. 6 is a cross-sectional schematic diagram of the lab-on-a-chip of FIG. 5 after at least some generation of gas has occurred.

FIGS. 5 and 6 depict an alternative embodiment where fluid movement can be useful on a lab-on-a-chip system. For example, the production of gas bubbles can effectuate the movement of a fluid, such as a reaction fluid. If the electrolyte is the fluid to be moved, this can be accomplished directly by forming gas bubbles and displacing the electrolyte fluid though a window or opening. If not, the formation of gas bubbles in the electrolytic fluid can displace a second fluid, as long as the two fluids are immiscible or a barrier is placed between the fluids, e.g., membrane or gas barrier. An advantage realized by such an embodiment is that the amount and rate of fluid ejection can be controlled by controlling the current flow.

Specifically, FIGS. 5 and 6 depict a lab-on-a-chip system 50 for movement of a reaction fluid 52. A housing 12 defines the electrolytic fluid chamber 18, reaction fluid-containing opening 54, and a reaction chamber 56. The housing 12 is integrated with a chip substrate 11 that carries active circuitry 13a, 13b. Active circuitry 13b carries power to the anode 14 and the cathode 16. By powering the anode 14 and the cathode 16 appropriately across electrolyte fluid present in the electrolytic fluid chamber 18, one or more gas bubble(s) 40 within the fluid chamber 18 can be generated, and the electrolytic fluid can act to inject a reaction fluid 52 into a reaction chamber 56. In other words, in the embodiment shown, the gas merely displaces the electrolytic fluid that, in turn, pushes behind the reaction fluid 52. In this embodiment, the electrolytic fluid and the reaction fluid are immiscible fluids, though this is not required. For example, a membrane could be present as described with respect to FIGS. 3 and 4, and the gas could be used to displace the reaction fluid 52.

Port 59 can be used to insert a reagent into the reaction chamber. Before, after, or simultaneously upon insertion of the reagent, by injecting an appropriate amount of reaction fluid 52 into the reaction chamber, a reaction can be carried out and reported to a computer (not shown). Alternatively, port 59 can be plugged when desired, or can be used to vent generated gases. Additionally, a sensor 58 can be present in the reaction chamber 56 that is configured to sense a reaction and transport the information to the active circuitry 13a through a metal trace 57, for example.

Figure 7:
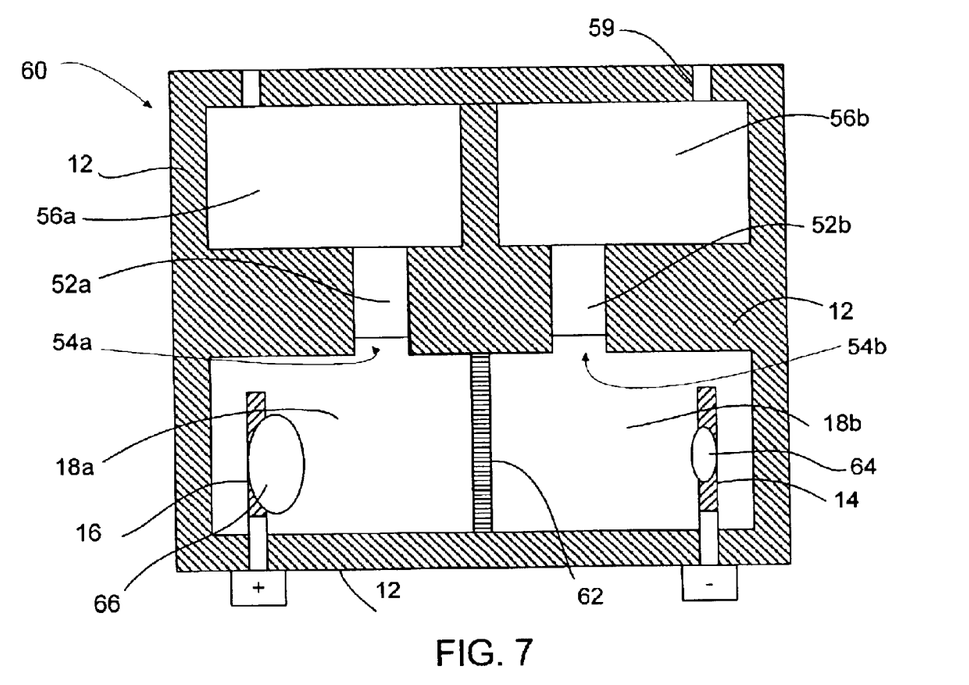
FIG. 7 is a cross-sectional schematic diagram of an electrolysis cell that can be present on a lab-on-a-chip, wherein the electrolysis cell is configured for injection of multiple fluids into a chamber in accordance with an embodiment of the present invention.
Figure 8:
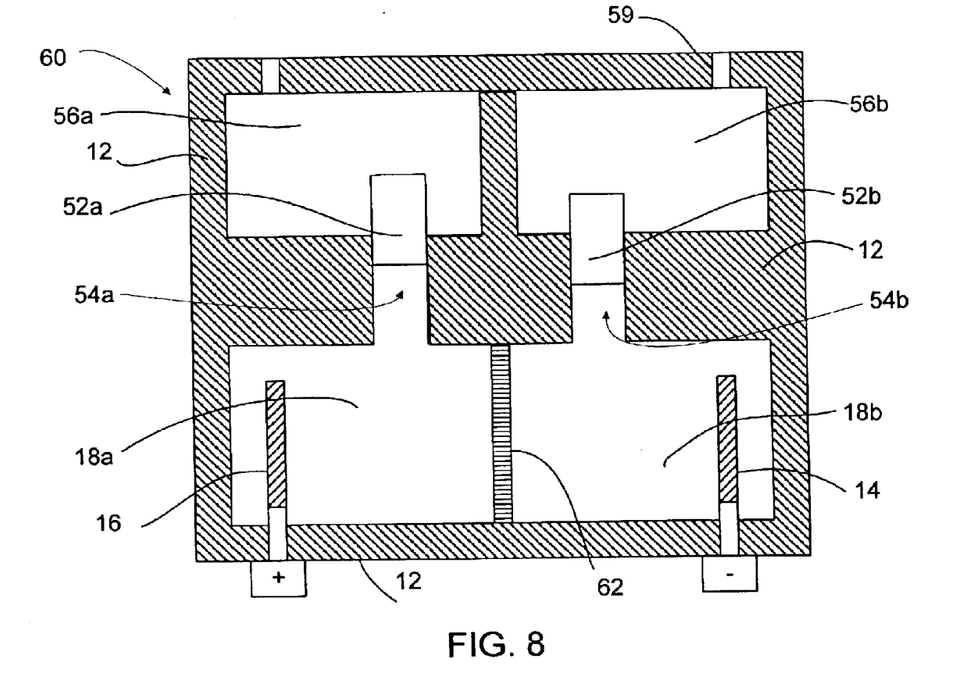
FIG. 8 is a cross-sectional schematic diagram of the electrolysis cell of FIG. 7 after at least some generation of gas has occurred.

In a similar embodiment, FIGS. 7 and 8 show a system 60 for movement of one or more reaction fluids 52 through two separate openings. Though the chip substrate and the active circuitry are not shown, they can be present as previously shown and described. Again, a housing 12 defines the fluid chamber 18, reaction fluid-containing opening 54, and a reaction chamber 56. The anode 14 and the cathode 16 in the present embodiment are separated by a membrane 62 that can be permeable to desired ions, and maintain a pressure differential. Thus, a first gas bubble 64 that is formed at the anode 14 will displace a first amount of electrolytic fluid, and a second gas bubble 66 that is formed at the cathode 16 will displace a second amount of electrolytic fluid. Upon displacement of the electrolytic fluid on either or both sides of the membrane, reaction fluids 52a, 52b can be displaced, and thus, injected into reaction chambers 56a, 56b at desired ratios. Though an immiscible fluid embodiment is shown, other arrangements would be ascertainable to one skilled in the art after considering the present disclosure.

The embodiment shown in FIGS. 7 and 8 provide some desired advantages, including the fact that the ratio of ejection of two different liquid reactants can be held constant if the evolved gases are held separately. This is one purpose for including the ionic member or membrane 62 between the two electrodes 14, 16. Such a membrane would allow for ion or electron flow, but would also prevent gas combination and pressure equalization. Additionally, with the use of certain electrode elements, electrolysis reactions can be reversible, e.g., gas bubbles can be grown, polarity can be reversed, and the bubbles can be consumed, thereby withdrawing the reaction fluids 52a, 52b.

Considering the above embodiments as exemplary, there are several advantages provided by the present invention. For example, the use of electrolysis can provide for the generation of two (or more) independent gas bubbles whose size can be held in a substantially exact ratio on a chip. This feature is not as readily available with thermally created bubbles. Additionally, the use of electrolysis to generate bubbles at a precisely determined time and rate can also be an advantage in a lab-on-a-chip environment. This can be accomplished by controlling the electric charge in the electrolytic fluid. The bubbles can then be used to provide useful work in the lab-on-a-chip at an appropriate time and place. Next, one can use electrolysis to generate bubbles on a chip of various sizes, again by varying the amount of electricity applied externally to the chip. In another embodiment, if there is a need to utilize a highly corrosive or reactive gas or liquid in a lab-on-a-chip environment, it can be created at the time of need. In other words, a needed gas or liquid can be stored in the form of its more benign precursor components, e.g. as an electrolyte fluid, thus increasing chip reliability and storage life. As described above, electrolytically produced gas bubbles can be used to create pressure, thereby causing fluid displacement and flow, e.g., for mixing fluids, for reacting fluids, for moving secondary fluids, etc.

Figure 9:
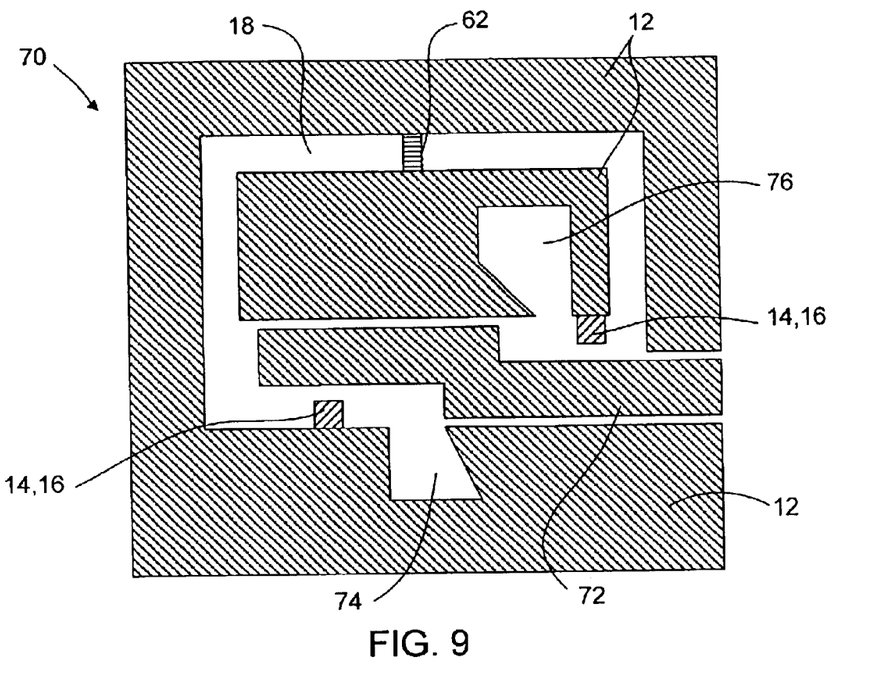
FIG. 9 is a cross-sectional schematic diagram of an electrolysis cell that can be present on a lab-on-a-chip, wherein the electrolysis cell is configured for moving a mechanical object in accordance with an embodiment of the present invention.
Figure 10:
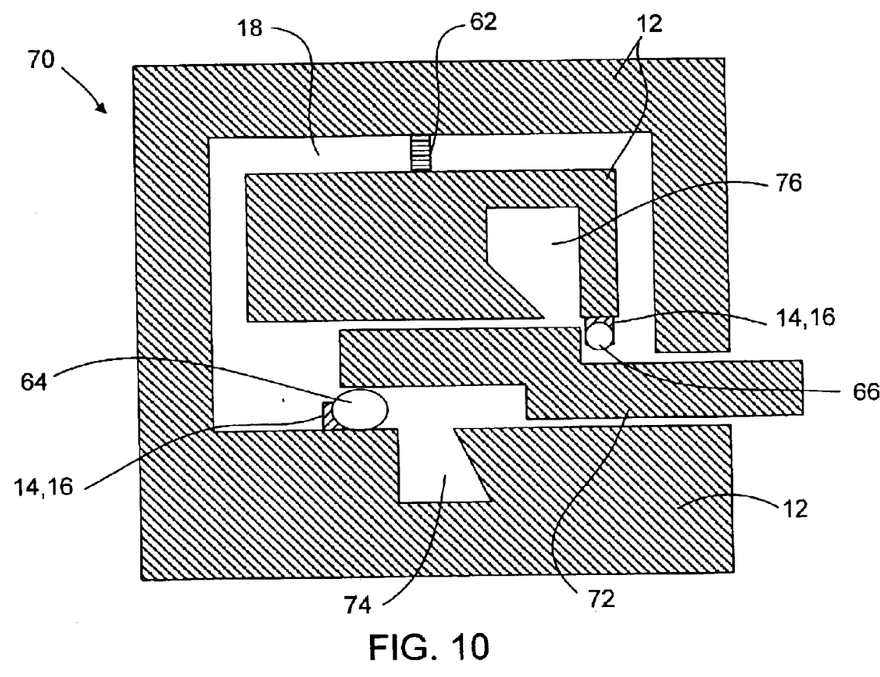
FIGS. 10–12 are cross-sectional schematic diagrams of the electrolysis cell of FIG. 9 at different points in time in a sequence of events wherein movement of a mechanical object is cycled.
Figure 11:
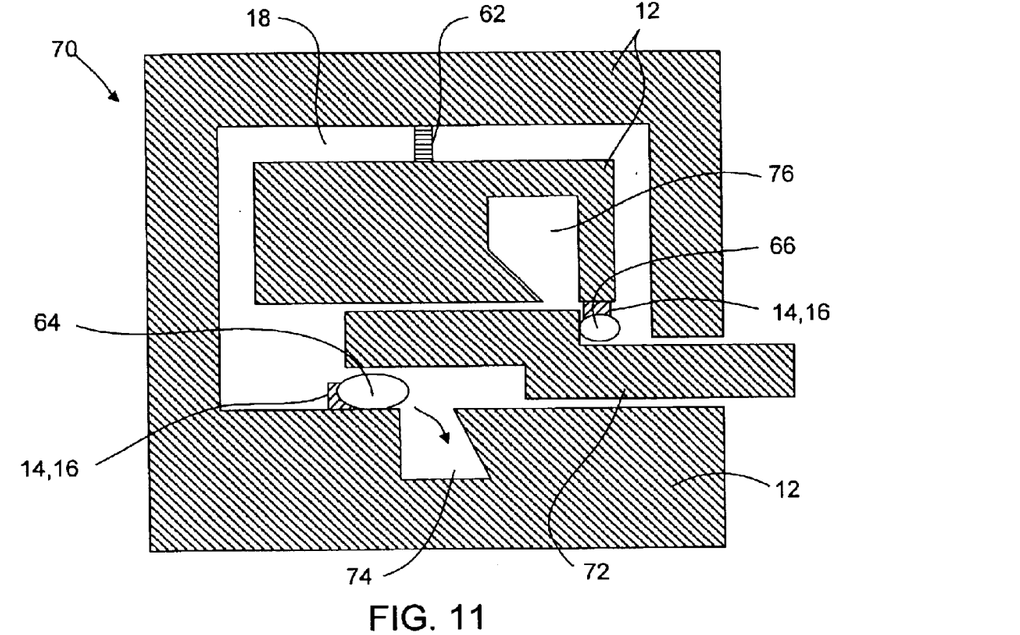
Figure 12:
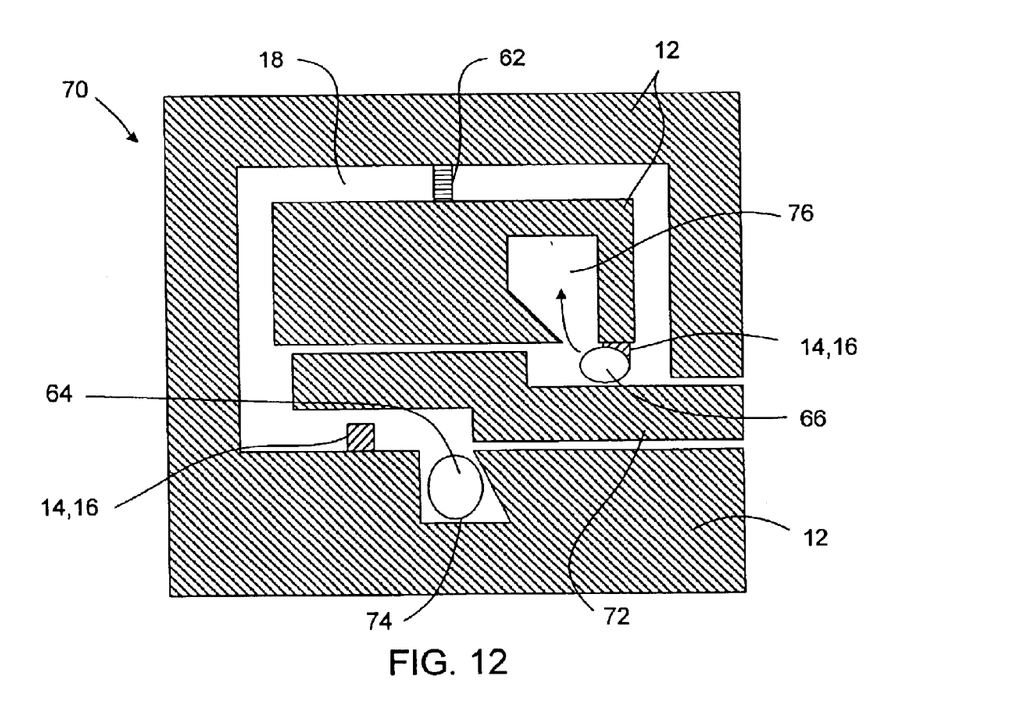

In FIGS. 9 to 12, a micromechanical device 70 for use on a lab-on-a-chip is shown that benefits from the electrolysis methods and systems of the present invention. Again, though the chip substrate and the active circuitry are not shown, it is understood that the system of FIGS. 9 to 12 are included as part of a lab-on-a-chip system which would necessarily include a chip substrate and active circuitry. Specifically, a plunger 72 or other mechanical device can be pushed out and retracted at a controlled rate by the electrolysis of an electrolytic fluid. FIG. 9 is provided to illustrate the device, and FIGS. 10 to 12 provide time interval depictions of gas bubbles 64, 66 acting on the electrolytic fluid, and ultimately, the plunger 72.

Specifically, with reference to FIG. 9, the system 70 comprises a housing 12 that defines a fluid chamber 18 containing an electrolyte fluid. A membrane 62 or some other ionic barrier is present so that a pressure differential can be created on either side of the fluid chamber 18. As part of the fluid chamber 18, a first bubble well 74 and a second bubble well 76 are also defined by the housing 12. Electrodes 14, 16 are positioned such that they are substantially fluidly separated by the membrane in a first direction, and by a movable plunger 72 in a second direction.

FIGS. 10 to 12 depict a result of growing gas bubbles of different volumes. Specifically, as the first gas bubble 64 forms and become larger in size than the second gas bubble 66, fluid is displaced. More specifically, the first bubble 64 causes the second bubble 66 to compress (storing energy in the form of pressure), in addition to moving the plunger 72. Once a full stroke has been achieved, the first gas bubble 64 is vented into the first bubble well 74, and the second bubble 66 then rapidly returns the plunger to its starting position. The effect of this embodiment is a slow out/fast return plunger. Such a plunger/gas bubble system can provide mechanical motion for a variety of mechanical functions, e.g., valving or varying liquid flow rates for example.

With these embodiments and figures in mind, an integrated lab-on-a-chip system for generating gases can comprise a substrate having active circuitry thereon, wherein the active circuitry is configured for communication with an electrolytic cell. The electrolytic cell can comprise various components. In this embodiment, the electrolytic cell will typically include a housing defining an electrolyte fluid chamber and a gas collection chamber. Additionally, an electrolyte fluid can be contained within the electrolyte fluid chamber, and positioned such that an anode and a cathode are in continuous contact with the electrolyte fluid. Thus, when the anode and cathode are energized, they can generate one or more gas(es) from the electrolyte fluid such that the gas is collected in the gas collection chamber. Further, a port can be present for enabling the use of the generated gas, e.g., configured for transporting the gas from the gas collection chamber to an application region for sustaining life, for use in a reaction, for providing fluid displacement, etc. The application region can be a chamber, such as a reaction chamber, or can be a region of space that is open to the atmosphere.

Communication between the active circuitry and the electrolytic cell is another feature of the present invention. This communication can be provided in one or more of several forms. For example, active circuitry can be used to communicate with the anode and the cathode. Alternatively, the communication can occur between the active circuitry and the generated gas itself. Communication can also occur between the active circuitry and a reaction product between the gas and a second reactant. Still further, communication can occur between the active circuitry and a secondary fluid, such as after displacement by a gas or a displaced electrolytic fluid. In these or other examples, the active circuitry can also act to provide power to components of the lab-on-a-chip, or can be used to interface with a computer.

In an alternative embodiment, an integrated lab-on-a-chip for conducting work with generated gases can comprise a substrate having active circuitry thereon, wherein the active circuitry is configured for communication with an electrolytic cell. The electrolytic cell can comprise a housing defining an electrolyte fluid chamber, and an electrolyte fluid contained within the electrolyte fluid chamber. An anode and a cathode can be positioned in contact with the electrolyte fluid, wherein the anode and cathode are configured for generating a gas from the electrolyte fluid. In one embodiment, the generated gas can be used to provide movement of a working fluid, for example. The working fluid can be any fluid that conducts work by fluid dynamics, reaction, or the like. For example, the working fluid can be the electrolyte fluid, or a second fluid. If a second fluid is the working fluid, one possible arrangement would include the displacement of the electrolytic fluid using the generated gas, wherein the electrolytic fluid pushes on the second fluid to conduct work or undergo a reaction.

In one embodiment, the working fluid can be a dielectric fluid movably disposed between capacitor plates. Alternatively, the working fluid can be a reactive fluid for chemical analysis or for the production of energy. In another embodiment, the electrolyte fluid can be the working fluid that causes mechanical movement of an object, e.g., a plunger, lever, rod or the like. The electrolytic fluid or the second fluid can also be configured to be moved by gas pressure. In one embodiment, the electrolyte fluid displacement is configured to cause movement of the second fluid. Other arrangements are also possible, as would be apparent to one skilled in the art after considering the present disclosure.

If a second fluid is used as the working fluid, then it is desirable to provide a system wherein the second fluid and the electrolytic fluid resist mixing. Thus, in one embodiment, the electrolytic fluid and the second fluid can be immiscible. In another embodiment, the second fluid can be separated from the electrolyte fluid by a barrier, such as one permeable to the gas but impermeable to the electrolyte fluid and the second fluid. Such a barrier can be a membrane that is impermeable to many liquids, as are known in the art.

As in the previous embodiment, communication between the active circuitry and electrolytic cell is important. Any of a number of communication interfaces can be used, such as communication between the active circuitry and the anode, the cathode, the gas, the electrolyte fluid, the working fluid, or other electrolytic cell components. Preferably, the active circuitry will be configured on the chip substrate such that it will be readable by a computer. However, the active circuitry can also be integrated with the electrolytic cell housing as well.

The reality of providing the ability to grow gases in an electrolytic cell to conduct work can also provide advantages upon a reversal of polarity of the anode and the cathode. By converting the anode to a cathode, and by converting the cathode to an anode, the ion flow can be reversed within the electrolytic fluid. This will provide a means of converting the generated gas back to the electrolytic fluid. Thus, by growing and consuming gas bubbles in the electrolytic cell, work can be done through displacement and retraction of fluids.

In an alternative embodiment, a method of generating gas in a lab-on-a-chip environment can comprise the steps of providing a substrate having active circuitry thereon, wherein at least a portion of the active circuitry is readable by a computer; (b) providing an electrolytic cell configured for communication with the active circuitry, wherein the electrolytic cell comprises an anode and a cathode in an electrolytic fluid bath; and (c) generating a gas in the electrolytic fluid bath by creating an electrical potential between the anode and the cathode through the electrolytic fluid bath. Additional method steps can also be carried out, depending on which embodiment is desired for use. For example, the method can further comprise the step of reacting the gas with a second reactant. Alternatively, the step of transporting the gas bubble to a gas collection chamber can also be carried out. Still further, the step of utilizing the gas to displace a fluid can provide some benefits. Appropriate fluids for displacement can include the electrolyte fluid, or some secondary fluid. In another embodiment, the step of moving a solid object mechanically by displacing a fluid with the generated gas can occur. Another use of the generated gas can include contributing the gas to an atmosphere to affect a living organism, such as bubbling oxygen gas into an environment where a cell culture is being grown.

Communication between the active circuitry and a component of the electrolytic cell is integral to the present invention. Such communication can occur at the anode, the cathode, in the gas, in the electrolyte fluid, in a secondary fluid such as a working fluid, or in/or at some other component of the electrolytic cell of the lab-on-a-chip.

With respect to additional details, the chip substrate and/or electrolysis cell housing can be comprised of silicon, glass, plastic, or ceramic. A chip substrate can be any size or configuration as is functional, but will typically be of a size for use with a computer, or of a size that is standard in the industry, e.g., silicon wafers are commercially available that are as large as about 6 inch or 8 inch diameters. In one embodiment, the electrolysis cell housing can be of a different material than the chip substrate. In another embodiment, the electrolysis cell housing can be of the same material as the chip substrate. Further, the housing can be deposited on the substrate, or can be etched into the substrate itself. These provide merely a few examples of the relationship between the chip substrate and the electrolysis cell housing, though others are certainly possible, and perhaps preferred.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

What is claimed is:

1. An integrated lab-on-a-chip system for generating gases, comprising a substrate having active circuitry deposited thereon, said active circuitry configured for communication with an electrolytic cell, said electrolytic cell, comprising:
   (a) a housing defining an electrolyte fluid chamber;
   (b) a gas collection chamber configured to receive a gas;
   (c) an electrolyte fluid contained within the electrolyte fluid chamber; and
   (d) an anode and a cathode positioned in contact with the electrolyte fluid, said anode and cathode configured for generating a gas from the electrolyte fluid, said gas collecting in the gas collection chamber.

2. A system as in claim 1, further comprising a port through the housing for enabling the use of the gas, wherein the port is configured for transporting the gas from the gas collection chamber to an application region.

3. A system as in claim 2, wherein the application region is a reaction chamber.

4. A system as in claim 2, wherein the application region is open to the atmosphere.

5. A system as in claim 1, wherein the active circuitry is configured for channeling power to the anode and the cathode, and for communication with the anode and the cathode.

6. A system as in claim 1, wherein the active circuitry is configured for communication with the gas.

7. A system as in claim 1, wherein the active circuitry is configured for communication with a reaction product generated by an interaction between the gas and a second reactant.

8. A system as in claim 1, wherein the active circuitry is configured for communication with a secondary fluid after interaction with the gas.

9. A system as in claim 1, wherein at least a portion of the active circuitry is configured for being read by a computer.

10. A system as in claim 1, wherein the gas is highly reactive or corrosive, and is not produced from the electrolyte fluid until the gas is desired for use.

11. A system as in claim 1, wherein the gas is generated at temperatures substantially below the boiling point of the electrolyte fluid.

12. A system as in claim 1, wherein at least two independent gases are generated.

13. An integrated lab-on-a-chip system for conducting work with generated gases, comprising a substrate having active circuitry deposited thereon, said active circuitry configured for communication with an electrolytic cell, said electrolytic cell, comprising:
   (a) a housing defining an electrolyte fluid chamber,
   (b) an electrolyte fluid contained within the electrolyte fluid chamber; and
   (c) an anode and a cathode positioned in contact with the electrolyte fluid, said anode and cathode configured for generating a gas from the electrolyte fluid, wherein generating said gas provides movement of a working fluid.

14. A system as in claim 13, wherein the working fluid is the electrolyte fluid.

15. A system as in claim 13, wherein the working fluid is a second fluid.

16. A system as in claim 15, wherein the second fluid is a dielectric fluid.

17. A system as in claim 15, wherein the second fluid is a reactive fluid.

18. A system as in claim 15, wherein the second fluid is immiscible with the electrolyte fluid.

19. A system as in claim 15, wherein the second fluid is separated from the electrolyte fluid by a barrier permeable to the gas, but impermeable to the electrolyte fluid and the second fluid.

20. A system as in claim 13, wherein the electrolyte fluid movement causes mechanical movement of an object.

21. A system as in claim 15, wherein gas pressure causes movement of the second fluid.

22. A system as in claim 15, wherein electrolyte fluid displacement causes movement of the second fluid.

23. A system as in claim 13, wherein the active circuitry is configured for channeling power to the anode and the cathode, and for communication with the anode and the cathode.

24. A system as in claim 13, wherein the active circuitry is configured for communication with the gas.

25. A system as in claim 13, wherein the active circuitry is configured for communication with the electrolyte fluid.

26. A system as in claim 13, wherein the active circuitry is configured for communication with the working fluid.

27. A system as in claim 13, wherein at least a portion of the active circuitry is configured for being read by a computer.

28. A system as in claim 13, wherein upon changing the polarity of the anode and the cathode, and upon reversing ion flow within the electrolytic fluid, generated gas is converted to the electrolytic fluid.

29. A system as in claim 13, wherein the gas is generated at temperatures substantially below the boiling point of the electrolyte fluid.

30. A system as in claim 13, wherein the movement of the working fluid provides a variable capacitance capacitor active circuitry element.

31. A system as in claim 13, wherein at least two independent gases are generated.

32. A method of generating gas in a lab-on-a-chip environment, comprising:
(a) providing a substrate having active circuitry thereon, at least a portion of said active circuitry being readable by a computer;
(b) providing an electrolytic cell configured for communication with the active circuitry, said electrolytic cell comprising an anode and a cathode in an electrolytic fluid bath; and
(c) generating a gas in the electrolytic fluid bath by creating an electrical potential between the anode and the cathode through the electrolytic fluid bath, said gas generation causing a function that is readable by said computer.

33. A method as in claim 32, further comprising the step of reacting the gas with a second reactant.

34. A method as in claim 32, further comprising the step of transporting the gas to a gas collection chamber.

35. A method as in claim 32, further comprising the step of maintaining the gas as a bubble to displace a fluid.

36. A method as in claim 35, wherein the fluid is the electrolyte fluid.

37. A method as in claim 35, wherein the fluid is a second fluid.

38. A method as in claim 32, further comprising the step of moving a solid object mechanically by displacing a working fluid with the gas.

39. A method as in claim 32, further comprising the step of contributing the gas to an atmosphere to affect a living organism.

40. A method as in claim 32, further comprising the step of carrying power to the anode and the cathode through the active circuitry.

41. A method as in claim 32, wherein the active circuitry is configured for communication with the gas.

42. A method as in claim 32, wherein the active circuitry is configured for communication with the electrolyte fluid.

43. A method as in claim 37, wherein the active circuitry is configured for communication with the second fluid.

44. A method as in claim 32, wherein the step of generating the gas occurs at a predetermined time and rate by controlling the electrical potential.

45. A method as in claim 32, further comprising the step of generating a second gas in the electrolytic fluid bath by creating an electrical potential between the anode and the cathode.

46. A method as in claim 32, wherein the gas is in the form of a bubble, and the size of the bubble is controllable by altering the electrical potential.

47. A method as in claim 32, wherein the gas is in the form of a bubble, and the bubble can be maintained for a period of at least 15 microseconds.

48. A method as in claim 32, wherein the step of generating the gas occurs at a temperature substantially below the boiling point of the electrolytic fluid bath.

* * * * *